United States Patent
Honda

(10) Patent No.: US 8,249,368 B2
(45) Date of Patent: Aug. 21, 2012

(54) IMAGE PROCESSING DEVICE

(75) Inventor: Hidenari Honda, Tokyo (JP)

(73) Assignee: Olympus Corporation, Tokyo (JP)

( * ) Notice: Subject to any disclaimer, the term of this patent is extended or adjusted under 35 U.S.C. 154(b) by 940 days.

(21) Appl. No.: 12/275,771

(22) Filed: Nov. 21, 2008

(65) Prior Publication Data

US 2009/0141989 A1 Jun. 4, 2009

Related U.S. Application Data

(63) Continuation of application No. PCT/JP2007/060504, filed on May 23, 2007.

(30) Foreign Application Priority Data

May 23, 2006 (JP) ................................. 2006-142416

(51) Int. Cl.
*G06K 9/36* (2006.01)
*G06K 9/40* (2006.01)

(52) U.S. Cl. ........ 382/232; 382/260; 382/233; 382/250; 382/274; 348/384.1

(58) Field of Classification Search ................... 382/232, 382/233, 246, 245, 250, 251, 274, 260; 345/555; 348/384.1, 440.1; 358/426.01, 426.16; 375/122, 375/240.01, 240.16

See application file for complete search history.

(56) References Cited

U.S. PATENT DOCUMENTS

| 6,798,834 | B1 | 9/2004 | Murakami et al. | |
| 7,796,831 | B2 * | 9/2010 | Tanaka | 382/274 |
| 7,944,457 | B2 * | 5/2011 | Lin et al. | 345/690 |
| 2004/0240554 | A1 * | 12/2004 | Murakami et al. | 375/240.16 |
| 2005/0105807 | A1 | 5/2005 | Suino et al. | |
| 2006/0178759 | A1 * | 8/2006 | Koehler | 700/18 |
| 2007/0014354 | A1 * | 1/2007 | Murakami et al. | 375/240.08 |

FOREIGN PATENT DOCUMENTS

| JP | 06-334985 | 12/1994 |
| JP | 7-222145 | 8/1995 |
| JP | 10-108197 | 4/1998 |
| JP | 2004-321603 | 11/2004 |
| JP | 2004-337596 | 12/2004 |
| JP | 2005-94578 | 4/2005 |

(Continued)

OTHER PUBLICATIONS

Supplementary European Search Report dated Sep. 30, 2011 from corresponding European Application No. EP 07 74 3938.8.

(Continued)

*Primary Examiner* — Ali Bayat
(74) *Attorney, Agent, or Firm* — Scully, Scott, Murphy & Presser, P.C.

(57) ABSTRACT

In this image processing device, an image processing portion 102 performs a predetermined pre-processing on first image data and outputs it as second image data. A judging portion 104 that judges the degree of importance of the first image data on the basis of the characteristics of a subject that is included in the first image data. A reducing portion 105 reduces the data amount of the second image data in accordance with that degree of importance and outputs it as third image data. According to this image processing device, by reducing the data amount of the second image data in accordance with the degree of importance of the first image data, it is possible to achieve greater reductions in the data amount as the degree of importance decreases. As a result, it is possible to more efficiently reduce the power consumption and time required when transferring image data after data reduction.

10 Claims, 14 Drawing Sheets

FOREIGN PATENT DOCUMENTS

| | | |
|---|---|---|
| WO | WO 2006/003647 A2 | 1/2006 |
| WO | WO 2006/046637 A1 | 5/2006 |

OTHER PUBLICATIONS

Deguchi, D., "An improvement of bronchoscope tracking by detecting bubble image", Journal of the Japan Society for Computer Aided Surgery, Dec. 30, 2005, pp. 431-432, vol. 7, No. 3.

Shonohara, R., "Kikanshi Navigation System ni Okeru camera Ugoki Suitei no Seido Kojo ni Kansuru Kenkyu", [online], Heisei 16 Nendo Joho Kogaku Course Sotsugyo Kenkyu Hokoku Yoshi, retrieval date Aug. 15, 2007, Internet URL:http://www.ice.nuie.nagova-thac.jp/thesis/2004/B/080130798.pdf.

International Search Report dated Aug. 28, 2007.

* cited by examiner

FIG. 6A

| FIELD IMPORTANCE | H DIRECTION PIXEL COUNT VALUE | H ENABLE |
|---|---|---|
| LOW | MODULO OF 4 = 0 | '1' |
| | OTHERWISE | '0' |
| MEDIUM | MODULO OF 2 = 0 | '1' |
| | OTHERWISE | '0' |
| HIGH | ALL VALUES | '1' |

FIG. 6B

| FIELD IMPORTANCE | V DIRECTION PIXEL COUNT VALUE | V ENABLE |
|---|---|---|
| LOW | MODULO OF 4 = 0 | '1' |
| | OTHERWISE | '0' |
| MEDIUM | MODULO OF 2 = 0 | '1' |
| | OTHERWISE | '0' |
| HIGH | ALL VALUES | '1' |

FIG. 9A

| FIELD IMPORTANCE | H UNIT COUNT VALUE | H PIXEL COUNT VALUE | H ENABLE |
|---|---|---|---|
| LOW | 0 | MODULO OF 4 = 0 | '1' |
| | | OTHERWISE | '0' |
| | 1 | MODULO OF 2 = 0 | '1' |
| | | OTHERWISE | '0' |
| | 2 | ALL VALUES | '1' |
| | 3 | MODULO OF 2 = 0 | '1' |
| | | OTHERWISE | '0' |
| | 4 | MODULO OF 4 = 0 | '1' |
| | | OTHERWISE | '0' |
| MEDIUM | 0 | MODULO OF 2 = 0 | '1' |
| | | OTHERWISE | '0' |
| | 1 | MODULO OF 2 = 0 | '1' |
| | | OTHERWISE | '0' |
| | 2 | ALL VALUES | '1' |
| | 3 | MODULO OF 2 = 0 | '1' |
| | | OTHERWISE | '0' |
| | 4 | MODULO OF 2 = 0 | '1' |
| | | OTHERWISE | '0' |
| HIGH | ALL VALUES | ALL VALUES | '1' |

FIG. 9B

| FIELD IMPORTANCE | V PIXEL COUNT VALUE | V UNIT COUNT VALUE | V ENABLE |
|---|---|---|---|
| LOW | 0 | MODULO OF 4 = 0 | '1' |
| | | OTHERWISE | '0' |
| | 1 | MODULO OF 2 = 0 | '1' |
| | | OTHERWISE | '0' |
| | 2 | ALL VALUES | '1' |
| | 3 | MODULO OF 2 = 0 | '1' |
| | | OTHERWISE | '0' |
| | 4 | MODULO OF 4 = 0 | '1' |
| | | OTHERWISE | '0' |
| MEDIUM | 0 | MODULO OF 2 = 0 | '1' |
| | | OTHERWISE | '0' |
| | 1 | MODULO OF 2 = 0 | '1' |
| | | OTHERWISE | '0' |
| | 2 | ALL VALUES | '1' |
| | 3 | MODULO OF 2 = 0 | '1' |
| | | OTHERWISE | '0' |
| | 4 | MODULO OF 2 = 0 | '1' |
| | | OTHERWISE | '0' |
| HIGH | ALL VALUES | ALL VALUES | '1' |

FIG. 11C

| FIELD IMPORTANCE | ... | | | | | HIGH | | | | |
|---|---|---|---|---|---|---|---|---|---|---|
| V PIXEL COUNT VALUE | 0 1 | ... | 0 1 | ... | 0 1 | | ... | 0 1 | ... | 0 1 |
| V UNIT COUNT VALUE | 0 | ... | 1 | ... | 2 | | ... | 3 | ... | 4 |
| V ENABLE | | | | | | | | | | |

IMAGE PROCESSING DEVICE

TECHNICAL FIELD

The present invention relates to an image processing device that processes image data.

This application is a continuation application based on a PCT Patent Application No. PCT/JP2007/060504, filed May 23, 2007, whose priority is claimed on Japanese Patent Application No. 2006-142416, filed May 23, 2006. The contents of both the PCT Application and the Japanese Application are incorporated herein by reference.

BACKGROUND ART

In conventional capsule endoscopes that are inserted in a body for observing organs, images are picked up by a charge coupled device (CCD) or the like, and after image processing such as white balance processing and gamma processing is performed on the images, the same compression is carried out on any image.

In contrast, in the image encoding device disclosed for example in Patent Document 1, a compression method is disclosed in which the center of the image is defined as a important region, and the periphery of the image is defined as a non-important region, whereby compression of differing extents is performed on the respective regions.

Patent Document 1: Japanese Unexamined Patent Application No. H06-334985

DISCLOSURE OF THE INVENTION

The present invention is an image processing device that includes a pre-processing portion that performs a predetermined pre-processing on first image data and outputs it as second image data; a judging portion that judges the degree of importance of the first image data on the basis of the characteristics of a subject that is included in the first image data; and a reducing portion that reduces the data amount of the second image data in accordance with the degree of importance and outputs it as third image data.

Also, the image processing device of the present invention is further provided with a dividing portion that divides the first image data into a plurality of areas, wherein the judging portion judges the degree of importance of each of the areas, and the reducing portion reduces the data amount of a corresponding region of the second image data in accordance with the degree of importance of each of the areas.

Also, the image processing device of the present invention is further provided with an image data cutout portion that cuts out a specified area from the first image data, wherein the judging portion judges the degree of importance of the specified area, and the reducing portion reduces the data amount of a corresponding region of the second image data in accordance with the degree of importance of the specified area.

Also, in the image processing device of the present invention, the judging portion is provided with a judging original data generating portion that generates judging original data for judging the degree of importance of the first image data and an importance judging portion that judges the degree of importance by comparing the judging original data and a threshold value.

Also, in the image processing device of the present invention, the judging original data generating portion generates the judging original data based on an average level of green in the first image data.

Also, in the image processing device of the present invention, the reducing portion is provided with a reduction processing portion that reduces the data amount of the second image data and a reduction rate setting portion that sets a reduction rate of the data amount corresponding to the degree of importance for the reduction processing portion.

Also, in the image processing device of the present invention, the reduction processing portion thins the second image data at a predetermined ratio, and the reduction rate setting portion sets the predetermined ratio.

Also, in the image processing device of the present invention, the reduction processing portion performs low-pass filter processing on the second image data, and the reduction rate setting portion sets a coefficient according to the low-pass filter processing.

Also, in the image processing device of the present invention, the reduction rate setting portion gradually changes the reduction rate from the periphery of an image to the center.

BRIEF DESCRIPTION OF THE DRAWINGS

FIG. 6A is a reference drawing that shows the generation conditions of enable in the first embodiment of the present invention.

FIG. 6B is a reference drawing that shows the generation conditions of enable in the first embodiment of the present invention.

FIG. 9A is a reference drawing that shows the generation conditions of enable in the second embodiment of the present invention.

FIG. 9B is a reference drawing that shows the generation conditions of enable in the second embodiment of the present invention.

FIG. 11C is a reference drawing that shows the waveform of the V enable in the case of the field importance being "high" in the second embodiment of the present invention.

Figure 1:
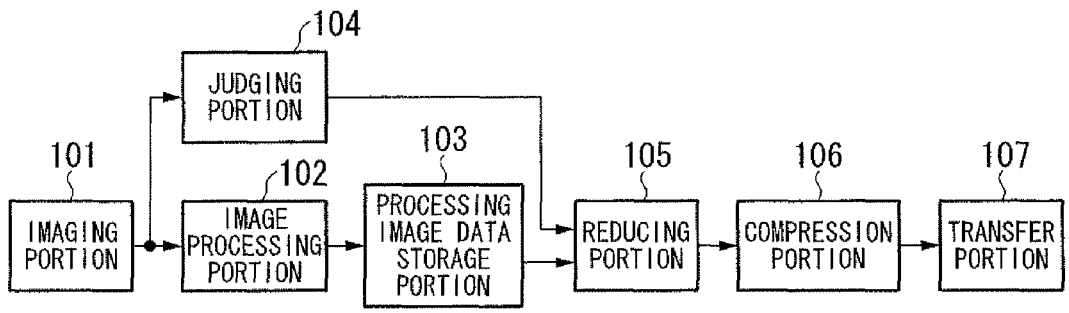
FIG. 1 is a block diagram that shows the constitution of the image processing device of the first embodiment of the present invention.

DESCRIPTION OF THE REFERENCE NUMERALS 102, 1202 image processing portion (pre-processing portion); 104, 1206 judging portion; 105, 1207 reducing portion; 201 judgment image data cutout portion; 202, 1501 importance index generating portion (judging original data generating portion); 203, 1502 importance judging portion; 301, 1601 reduction rate control signal generating portion (reduction rate setting portion); 302, 1602 reduction processing portion; 1205 dividing portion; 1704 LPF coefficient generating portion (reduction rate setting portion)

BEST MODE FOR CARRYING OUT THE INVENTION

Hereinbelow, embodiments of the present invention shall be described with reference to the appended drawings.
(First Embodiment)
First, a first embodiment of the present invention shall be described. An image processing device according to the present embodiment is an image processing device for a capsule endoscope. Based on the picked-up image of one field (partial region of a picked-up image in the present embodiment) among the picked-up images that are continuously imaged by the imaging element (imaging means) such as a CCD, it judges whether or not the picked-up image is important as an endoscope image for each field, and performs pixel thinning at a thinning rate in accordance with the judgment result. FIG. 1 shows the constitution of the image processing device according to the present embodiment. Hereinbelow, the general functions of the constitution of the present image processing device shall be described.

An imaging portion 101 performs image capture with a CCD or the like, and generates captured image data that is data of pixels that constitute the captured image. An image processing portion 102 performs spatial image processing (pre-processing) such as white balance processing and gamma processing on the captured image data, and generates processing image data that is data of the pixels that constitute the processing image. A processing image data storage portion 103 temporarily stores processing image data. A judging portion 104 judges the field importance on the basis of the characteristics of the subject using a portion of the captured image data as judgment image data for judging the field importance that shows whether or not the captured image of one field is important as an endoscope image.

A reducing portion 105 reduces the data amount of the processing image data by performing pixel thinning of the processing image data that is read from the processing image data storage portion 103 in accordance with the field importance and obtains reduced image data. A compression portion 106 compresses the reduced image data to obtain compressed image data. A transfer portion 107 transfers the compressed image data to the outside.

Figure 2:
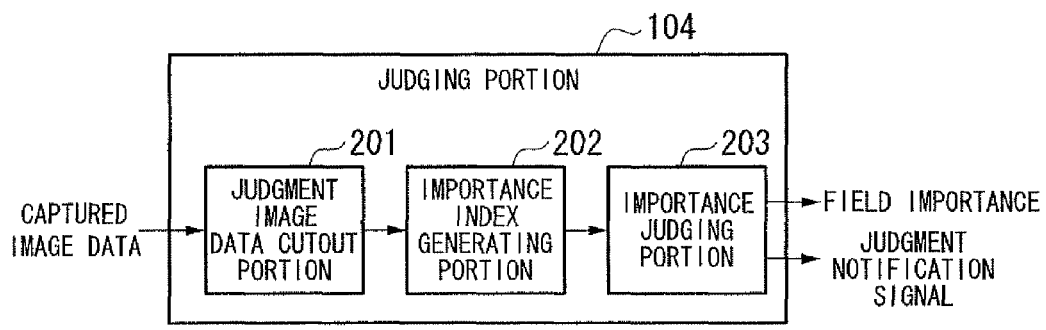
FIG. 2 is a block diagram that shows the constitution of the judging portion provided in the image processing device of the first embodiment of the present invention.

FIG. 2 shows the constitution of the judging portion 104. A judgment image data cutout portion 201 cuts out judgment image data from the captured image data. An importance index generating portion 202 generates a field importance index that is an index when judging the field importance of the captured image from the judgment image data. An importance judging portion 203 judges the field importance based on the field importance index.

Figure 3:
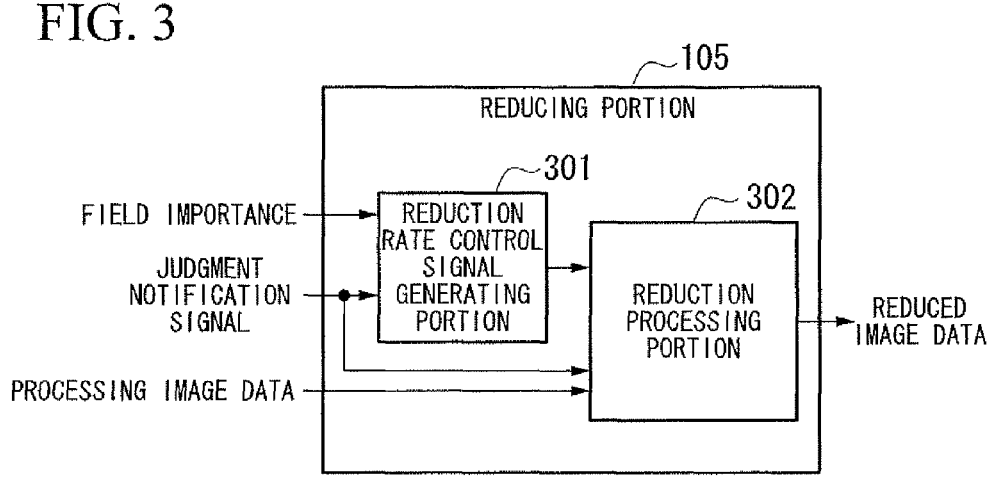
FIG. 3 is a block diagram that shows the constitution of the reducing portion provided in the image processing device of the first embodiment of the present invention.

FIG. 3 shows the constitution of the reducing portion 105. A reduction rate control signal generating portion 301 generates enable in relation to the pixel thinning of the processing image data, and outputs it as a reduction rate control signal. A reduction processing portion 302 performs pixel thinning of the processing image data according to the reduction rate control signal, and generates reduced image data. The thinning rate of the pixel thinning is set by the reduction rate control signal.

Figure 4:
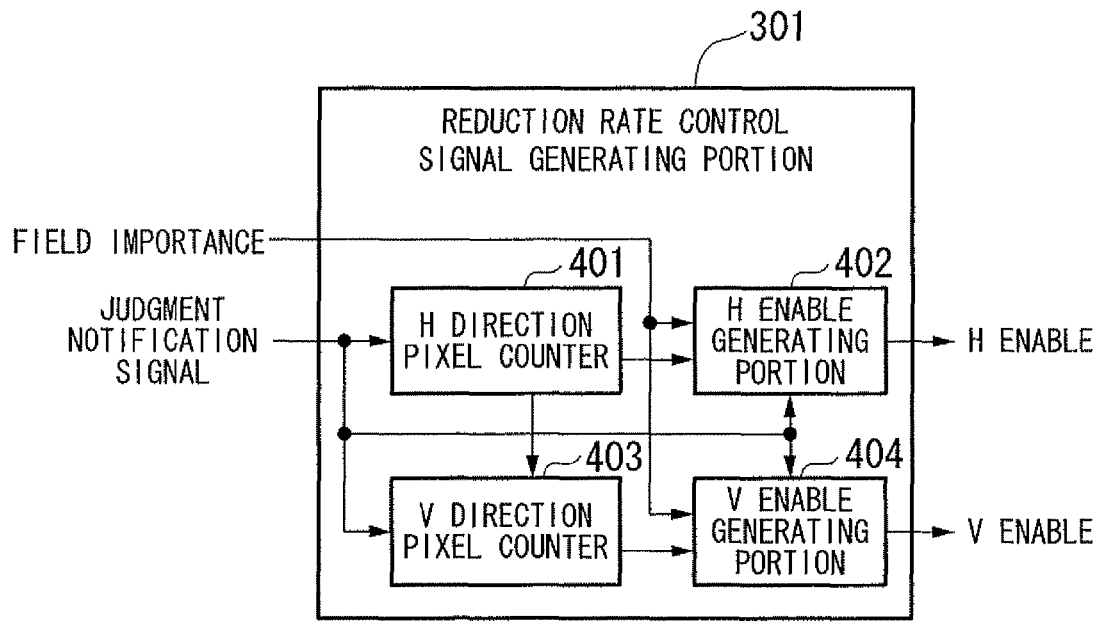
FIG. 4 is a block diagram that shows the constitution of the reduction rate control signal generating portion provided in the image processing device of the first embodiment of the present invention.

FIG. 4 shows the constitution of the reduction rate control signal generating portion 301. An H direction pixel counter 401 counts the number of pixels in the H direction (horizontal direction) of the processing image. An H enable generating portion 402 generates an enable in relation to pixel thinning in the H direction of a processing image. A V direction pixel counter 403 counts the number of pixels in the V direction (perpendicular direction) of a processing image. A V enable generating portion 404 generates an enable in relation to pixel thinning in the V direction of a processing image.

Next, the field importance in the present embodiment shall be described. In endoscope images, those which include many bubbles in the image are considered non-important images, while those which include few are considered important images. Also, there tends to be more G (green) components in images which contain many bubbles than images which contain few bubbles. Moreover, for example Japanese Unexamined Patent Application No. 2004-321603 and Japanese Unexamined Patent Application No. 2004-337596 disclose art that judges which organ is in an image that is currently being captured by calculating the average color of the image that is being captured. Therefore, by calculating the ratio of the average G level (green component level) of the picked-up image of one field and the average G level that is expected for the organ that is currently being imaged, it is possible to estimate the amount of bubbles that are contained in the picked-up image. For that reason, the present embodiment judges the field importance by this method.

Figure 5:
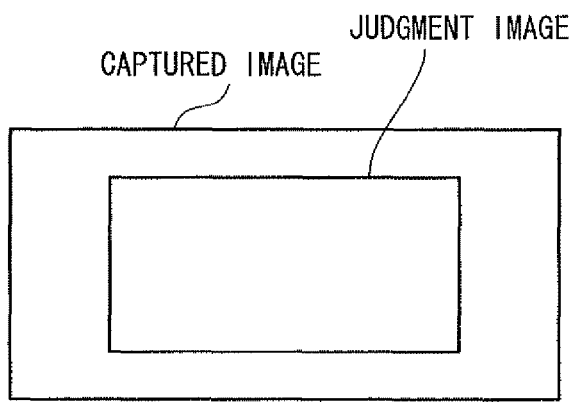
FIG. 5 is a reference drawing that shows the appearance of the cutout of the judging image data in the first embodiment of the present invention.

Next, the operation of the image processing device according to the present embodiment shall be described. The image processing portion 102 generates the processing image data by performing predetermined image processing on the captured image data that is obtained by the imaging portion 101, and once writes the processing image data in the processing image data storage portion 103. The judgment image data cutout portion 201 of the judging portion 104 generates judgment image data that is pixel data of a judgment image in which for example the periphery of the captured image has been as shown in FIG. 5.

The importance index generating portion 202, after calculating the average G level of the judgment image data of one field, calculates the ratio with the average G level that is expected for an organ to be observed that is set in advance, and outputs it as a field importance index (judging original data). The importance judging portion 203, by comparing the field importance index and a plurality of importance judgment threshold values set in advance, outputs the field importance by judging the field importance of the captured image (for example, one of the three levels of low, medium, high) at the end of one field and generates and outputs a judgment notification signal that shows that the field importance judgment of the captured image is complete.

The reduction rate control signal generating portion 301 in the reducing portion 105 generates a reduction rate control signal as follows in parallel with the processing image data being read out from the processing image data storage portion 103. When processing image data are read, pixel data of one line are read out in sequence from the pixel at the upper left of a captured image, after which the pixel data of the next line is read out in sequence from the pixel at the left end, and so on, whereby the pixel data of each line are read one by one.

The H direction pixel counter 401 in the reduction rate control signal generating portion 301 generates an H direction pixel count value that counts the pixels in the H direction in the processing image by performing a count for each reference timing with the judgment notification signal serving as a start trigger, and performing a reset at each counting of the number of pixels in the H direction of the processing image data. The V direction pixel counter 403 in the same manner generates a V direction pixel count value that is a count of the pixels in the V direction in the processing image by counting at the timing at which the H direction pixel count value is reset with the judgment notification signal serving as a start trigger, and performing a reset each time the V direction pixel number of the processing image is counted.

The H enable generating portion 402 generates an enable in relation to pixel thinning of H direction pixel data (called an H enable) from the field importance and H direction pixel count value for each pixel of the captured image. FIG. 6A shows the H enable generation conditions. In the case of the field importance being "low", when the remainder of dividing the H direction pixel count value by 4 is "0", the H enable is "1", and when other than that the H enable is "0". Also, in the case of the field importance being "medium", when the remainder of dividing the H direction pixel count value by 2 is "0", the H enable is "1", and when other than that the H enable is "0". Also, in the case of the field importance being "high", the H enable is "1" regardless of the H direction pixel count value.

The V enable generating portion 404 generates an enable (called a V enable) in relation to pixel thinning of V direction pixel data from the field importance and V direction pixel count value. FIG. 6B shows the V enable generation conditions. The V enable generation conditions are the same as the H enable generation conditions. By following the conditions for FIG. 6A and FIG. 6B, the enable is generated such that the lower the field importance, the higher the thinning rate.

The reduction processing portion 302 reads the processing image data from the processing image data storage portion 103 by having the judgment notification signal serve as a start trigger and sifts through the processing image data by validating processing image data when both the H enable and V enable are "1" and otherwise invalidating the processing image data. Thereby, data reduction is performed by pixel thinning of the processing image data to obtain reduced image data. The compression portion 106 generates compressed image data by compressing the reduced image data using JPEG or the like. The transfer portion 107 transfers the compressed image data from inside the body to outside the body. Outside the body, when expanding and playing back the compressed image data, the image data of the thinned pixel positions is found by interpolation.

As described above, in the present embodiment, the reduction rate of the processing image data is controlled according to the degree of importance of the captured image. By reducing greater amounts of data the lower the degree of importance of the data as in the present embodiment, it is possible to more efficiently reduce the power consumption and time required for transferring the image data to the outside after data reduction.

Also, by cutting out the judgment image data of a specified area from the captured image data and judging the degree of importance of the captured image using the judgment image data, it is possible to achieve a greater reduction in the amount of computation required for judging the degree of importance than the case of using all of the captured image data for judgment of the degree of importance. Also, it is possible to qualitatively judge degree of importance by generating a field importance index (judging original data) used for judgment of degree of importance and judging the degree of importance based on the result of comparing the field importance index and importance judgment threshold value.

(Second Embodiment)

Next, a second embodiment of the present invention shall be described. With respect to the image processing device according to the first embodiment that judges the degree of importance for each field of a captured image and performs pixel thinning at a thinning rate in accordance with the judgment result, the image processing device according to the present embodiment is one that combines the functions of performing pixel thinning at a thinning rate that differs at the center portion and peripheral portion of the captured image.

Figure 8:
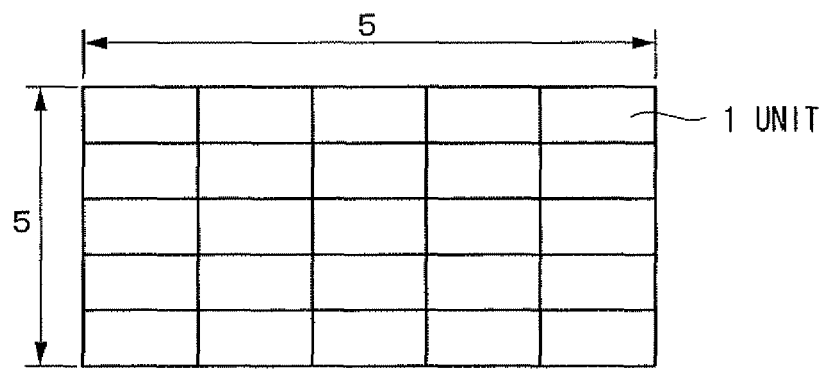
FIG. 8 is a reference drawing that shows the appearance of the division of the processing image in the second embodiment of the present invention.

Hereinbelow, pixel thinning of the processing image data in the present embodiment shall be described. A known characteristic of human visual perception is to focus more on the center portion of an image than the periphery thereof. Therefore, by utilizing this visual perception characteristic in the present embodiment, the center portion of a processing image is regarded as an important region while the periphery is regarded as a non-important region. Pixel thinning of the processing image data is then performed by varying the pixel thinning rate of the important region and the non-important region. When performing pixel thinning of a processing image, in order to perform pixel thinning at a thinning rate that differs between the center portion and periphery of a processing image, the processing image is divided into 5×5 regions as shown in FIG. 8, with each division unit being called a unit.

Figure 7:
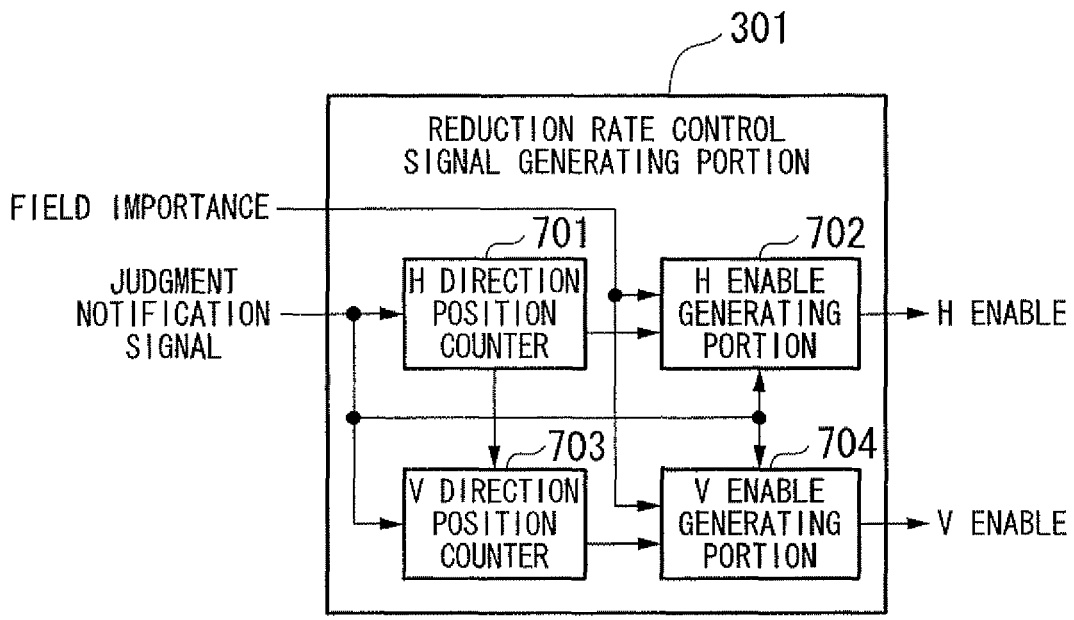
FIG. 7 is a block diagram that shows the constitution of the reduction rate control signal generating portion provided in the image processing device of the second embodiment of the present invention.

The image processing device according to the present embodiment replaces the constitution of the reduction rate control signal generating portion 301 in the first embodiment shown in FIG. 3 with constitution shown in FIG. 7, and in other respects is similar to the first embodiment. Therefore, descriptions of constitutions that are the same as the first embodiment shall be omitted, and the function of the constitution of only the reduction rate control signal generating portion 301 shall be described. In FIG. 7, an H direction position counter 701 counts information in relation to the position in the H direction of the processing image.

An H enable generating portion 702 generates an enable in relation to pixel thinning in the H direction of the processing image. A V direction position counter 703 counts information in relation to the position in the V direction of the processing image. A V enable generating portion 704 generates an enable in relation to pixel thinning in the V direction of the processing image.

Next, the operation of the image processing device according to the present embodiment shall be described. The reading of processing image data from the processing image data storage portion 103 is the same as in the first embodiment, and the reduction rate control signal generating portion 301 generates a reduction rate control signal as shown below in parallel with processing image data being read from the processing image data storage portion 103.

The H direction position counter 701 generates an H pixel count value that counts the pixels in the H direction in a unit by performing a count for each reference timing with the judgment notification signal serving as a start trigger and performing a reset at each counting of the number of pixels in the H direction of the unit. Also, the H direction position counter 701 in parallel with this generates an H unit count value that counts the units in the H direction in the processing image by performing a count at the timing at which the H pixel count value is reset with the judgment notification signal serving as a start trigger, with the H pixel count value being reset at each counting of the total number of pixels in the H direction of the processing image. Also, the H direction position counter 701 generates an increment signal that shows that the counting of the pixel number in the H direction of the processing image has been completed during resetting of the H unit count value.

Figure 10A:
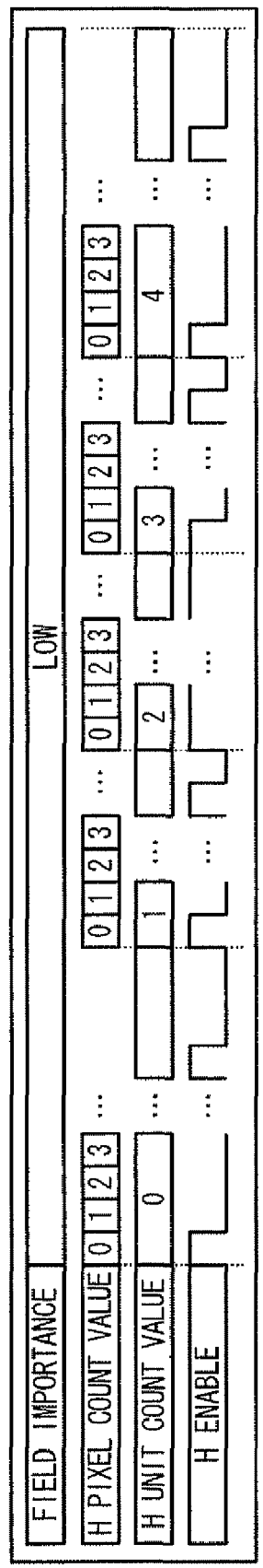
FIG. 10A is a reference drawing that shows the waveform of the H enable in the case of the field importance being "low" in the second embodiment of the present invention.
Figure 10B:
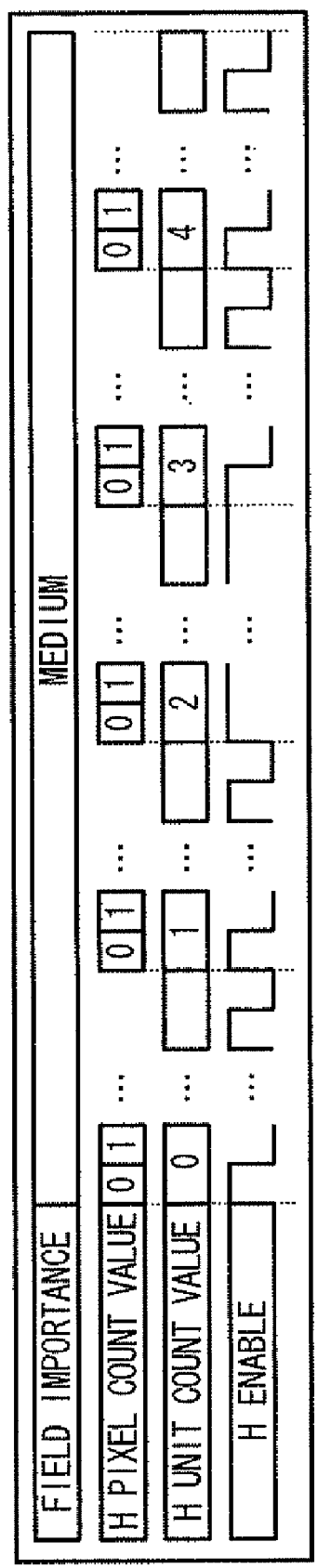
FIG. 10B is a reference drawing that shows the waveform of the H enable in the case of the field importance being "medium" in the second embodiment of the present invention.
Figure 10C:
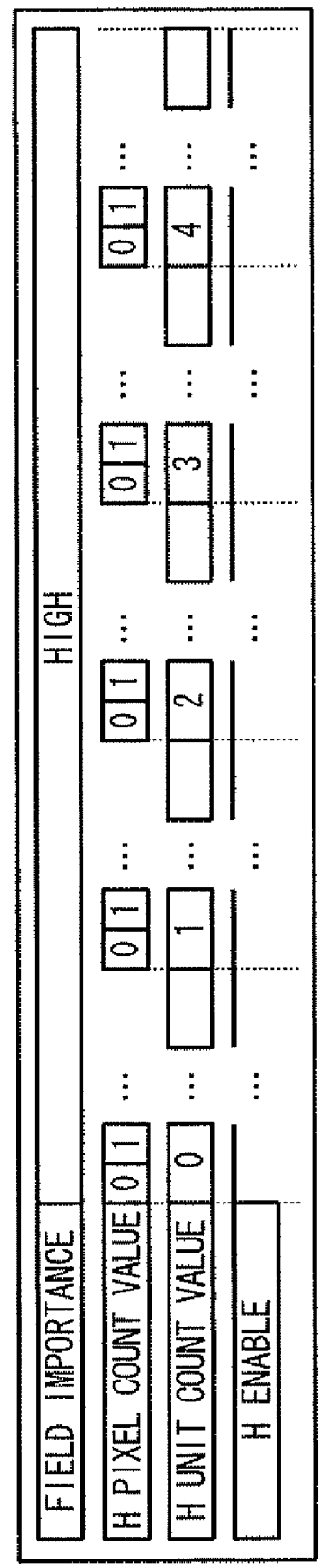
FIG. 10C is a reference drawing that shows the waveform of the H enable in the case of the field importance being "high" in the second embodiment of the present invention.

The H enable generating portion 702 generates an enable in relation to pixel thinning of H direction pixel data (called the H enable) from the field importance, the H unit count value and the H pixel count value. FIG. 9A shows the H enable generation conditions. FIG. 10A to FIG. 10C show the waveform of the H enable that is generated according to the conditions of FIG. 9A. FIG. 10A shows the waveform of the H enable in the case of the field importance being "low", FIG. 10B shows the waveform of the H enable in the case of the field importance being "medium", and FIG. 10C shows the waveform of the H enable in the case of the field importance being "high".

The V direction position counter 703 generates a V pixel count value that counts the pixels in the V direction in a unit by performing a count at each increment with the judgment notification signal serving as a start trigger and performing a reset at each counting of the number of pixels in the V direction of the unit. Also, the V direction position counter 703 in parallel with this generates a V unit count value that counts the units in the V direction in the processing image by performing a count at the timing at which the V pixel count value is reset with the judgment notification signal serving as a start trigger, with the V pixel count value being reset at each counting of the total number of pixels in the V direction of the processing image.

Figure 11A:
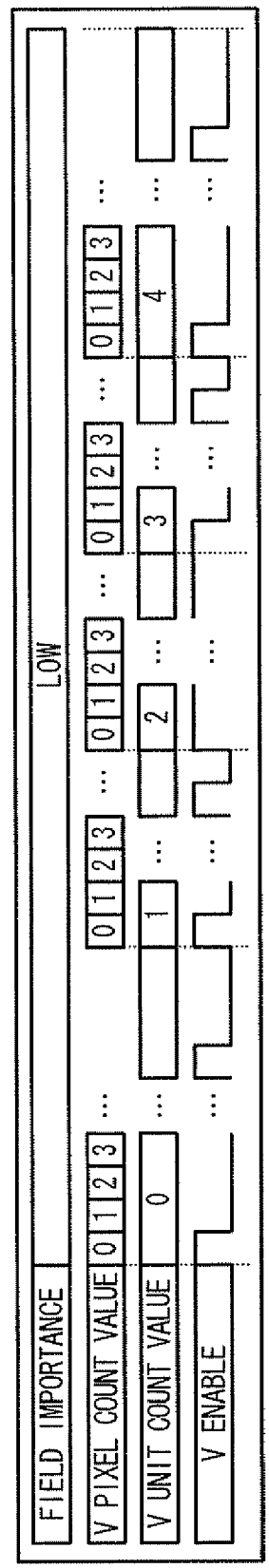
FIG. 11A is a reference drawing that shows the waveform of the V enable in the case of the field importance being "low" in the second embodiment of the present invention.
Figure 11B:
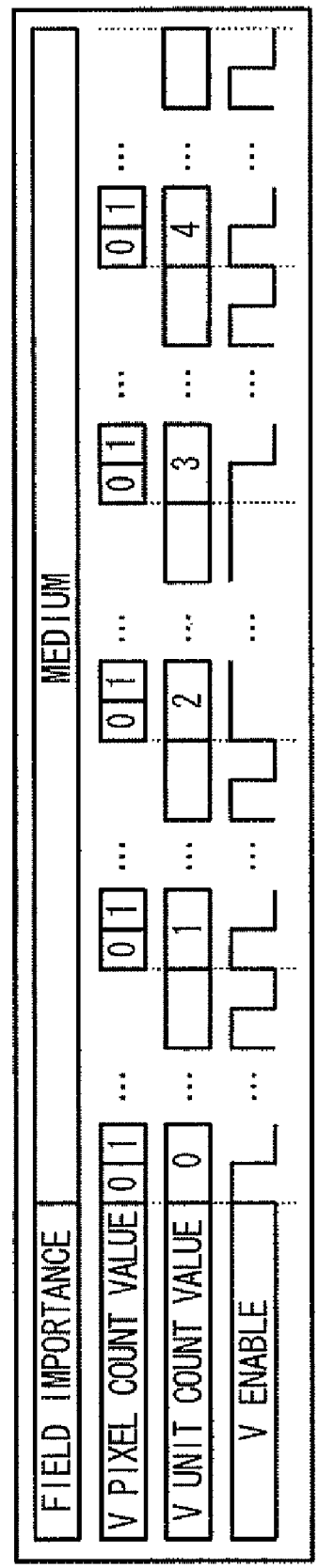
FIG. 11B is a reference drawing that shows the waveform of the V enable in the case of the field importance being "medium" in the second embodiment of the present invention.

The V enable generating portion 704 generates an enable in relation to pixel thinning of V direction pixel data (called the V enable) from the field importance, the V unit count value and the V pixel count value. FIG. 9B shows the H enable generation conditions. FIG. 11A to FIG. 11C show the waveform of the V enable that is generated according to the conditions of FIG. 9B. FIG. 11A shows the waveform of the V enable in the case of the field importance being "low", FIG. 11B shows the waveform of the V enable in the case of the field importance being "medium", and FIG. 11C shows the waveform of the V enable in the case of the field importance being "high".

By generating enables according to the conditions of FIG. 9A and FIG. 9B, enables are generated so that the thinning rate of the overall image increases as the field importance decreases, and in the case of the degree of importance of the image not being high, the thinning rate gradually decreases from the periphery to the center of the image. Thereafter, pixel thinning of the processing image data, generation of compressed image data, and transfer of the compressed data are performed in the same process as the first embodiment.

According to the aforementioned embodiment, it is possible to more efficiently reduce the power consumption and time required for transferring the image data to the outside after data reduction, similarly to the first embodiment. Also, in the case of the important region and non-important region in the captured image being known in advance (with the center portion being the important region and the periphery being the non-important region in the present embodiment), it is possible to control the reduction rate of data in accordance with the degree of importance of the captured image itself and also set a reduction rates that differ at the important region and non-important region, and so it is possible to even more efficiently reduce the power consumption and time required for transferring the image data to the outside after data reduction. Also, by gradually changing the reduction rate of the data, it is possible to smoothly alter the image quality and possible to prevent visual unnaturalness.

(Third Embodiment)

Next, a third embodiment of the present invention shall be described. The image processing device according to the present embodiment judges whether or not the capture image is important as an endoscope image for each region that divides the captured image of one field, and performs strong low pass filter (LPF) processing in accordance with the Judgment result at each region.

Figure 12:
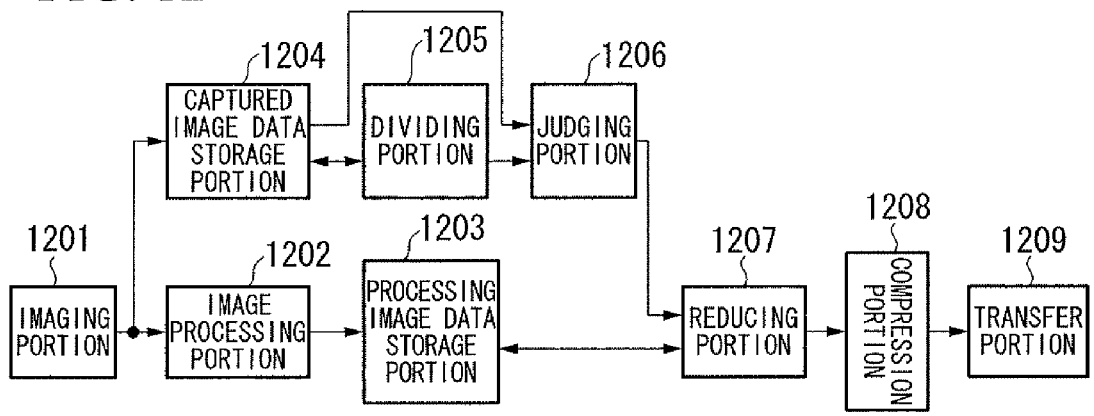
FIG. 12 is a block diagram that shows the constitution of the image processing device of the third embodiment of the present invention.

FIG. 12 shows the constitution of the image processing device according to the present embodiment. Hereinbelow, the general functions of the constitution of the present image processing device shall be described. An imaging portion 1201 performs image capture with a CCD or the like, and generates captured image data that is data of pixels that constitute the captured image. An image processing portion 1202 performs spatial image processing such as white balance processing and gamma processing on the captured image data, and generates processing image data that is data of the pixels that constitute the processing image. A processing image data storage portion 1203 temporarily stores processing image data.

Figure 13:
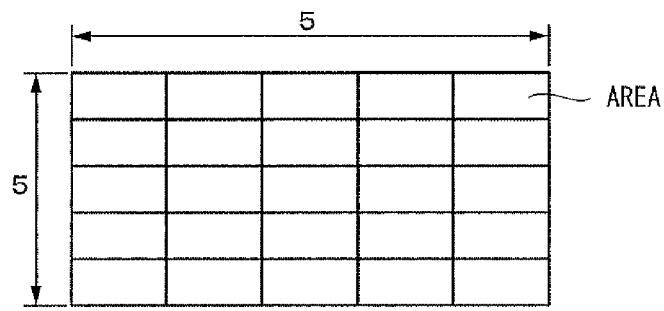
FIG. 13 is a reference drawing that shows the appearance of division of a captured image in the third embodiment of the present invention.

A captured image data storage portion 1204 temporarily stores captured image data. A dividing portion 1205 divides the captured image data that is read from the captured image data storage portion 1204 and, in order to judge the degree of importance of each division region, generates a division control signal for dividing the captured image into, for example, 5×5 regions (areas) as shown in FIG. 13. A judging portion 1206 judges the area importance that shows whether or not the captured image of the area unit is important as an endoscope image from the captured image data that is read from the captured image data storage portion 1204 and a division control signal.

A reducing portion 1207 reduces the data amount of the processing image data by performing LPF processing of the processing image data that is read from the processing image data storage portion 1203 according to the area importance and obtains reduced image data. A compression portion 1208 compresses the reduced image data to obtain compressed image data. A transfer portion 1209 transfers the compressed image data to the outside.

Figure 14:
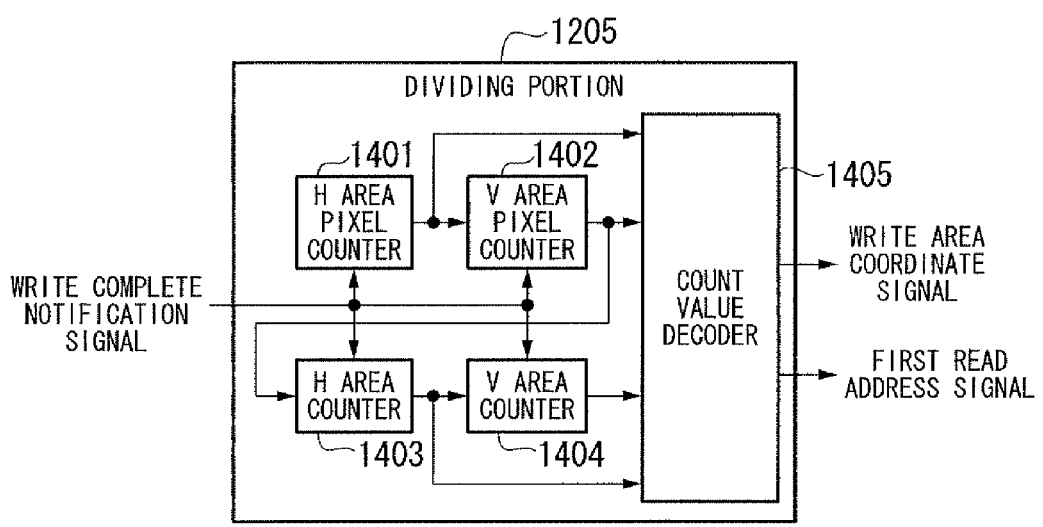
FIG. 14 is a block diagram that shows the constitution of the dividing portion that is provided in the image processing device in the third embodiment of the present invention.

FIG. 14 shows the constitution of the dividing portion 1205. An H area pixel counter 1401 generates an H area pixel count value that counts the pixels in the H direction of the area. A V area pixel counter 1402 generates a V area pixel count value that counts the pixels in the V direction of the area. An H area counter 1403 generates an H area count value that counts the areas in the H direction of the captured imaged. A V area counter 1404 generates a V area count value that counts the areas in the V direction of the captured image. A count value decoder 1405 decodes the H area pixel count value, the V area pixel count value, the H area count value and the V area count value, and generates a write area coordinate signal and a read address signal described below.

Figure 15:
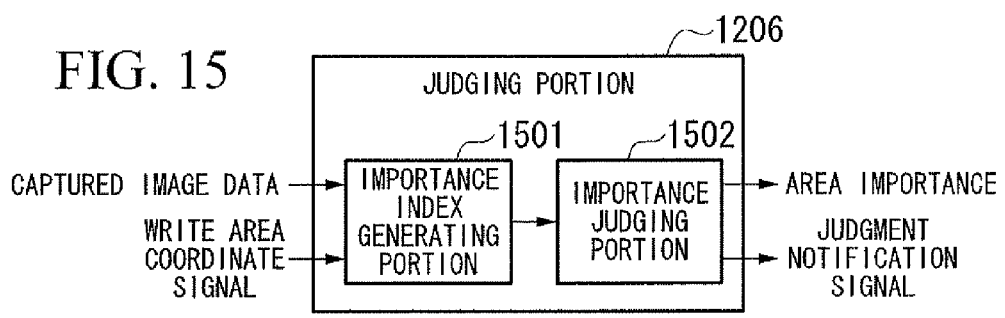
FIG. 15 is a block diagram that shows the constitution of the judging portion that is provided in the image processing device in the third embodiment of the present invention.

FIG. 15 shows the constitution of the judging portion 1206. An importance index generating portion 1501 generates an area importance index that is an index when judging the area importance of the captured image from the judgment image data. An importance judging portion 1502 judges the area importance based on the area importance index.

Figure 16:
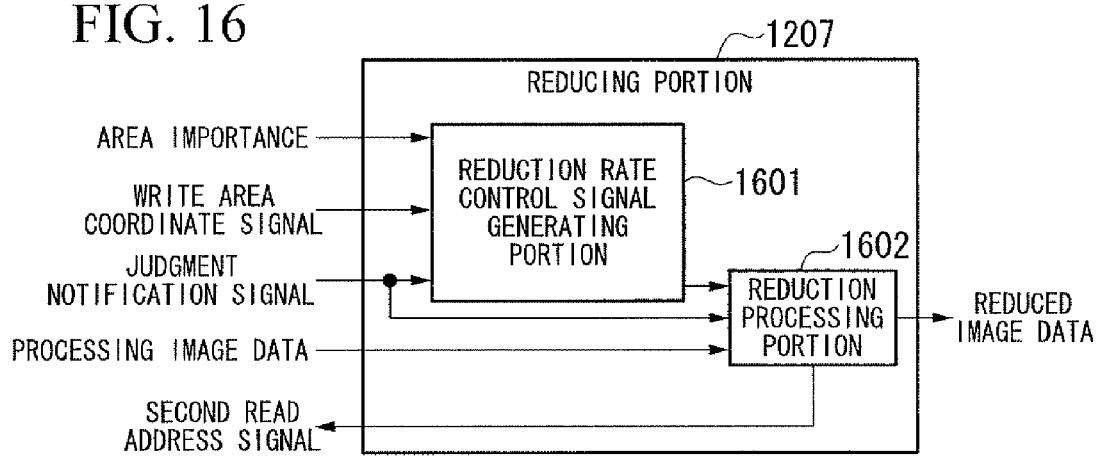
FIG. 16 is a block diagram that shows the constitution of the reducing portion that is provided in the image processing device in the third embodiment of the present invention.

FIG. 16 shows the constitution of the reducing portion 1207. A reduction rate control signal generating portion 1601 generates an LPF coefficient when performing LPF processing on the processing image data based on the area importance, and outputs it as a reduction rate control signal. A reduction processing portion 1602 performs LPF processing of the processing image data in accordance with the reduction rate control signal, and generates reduced image data.

Figure 17:
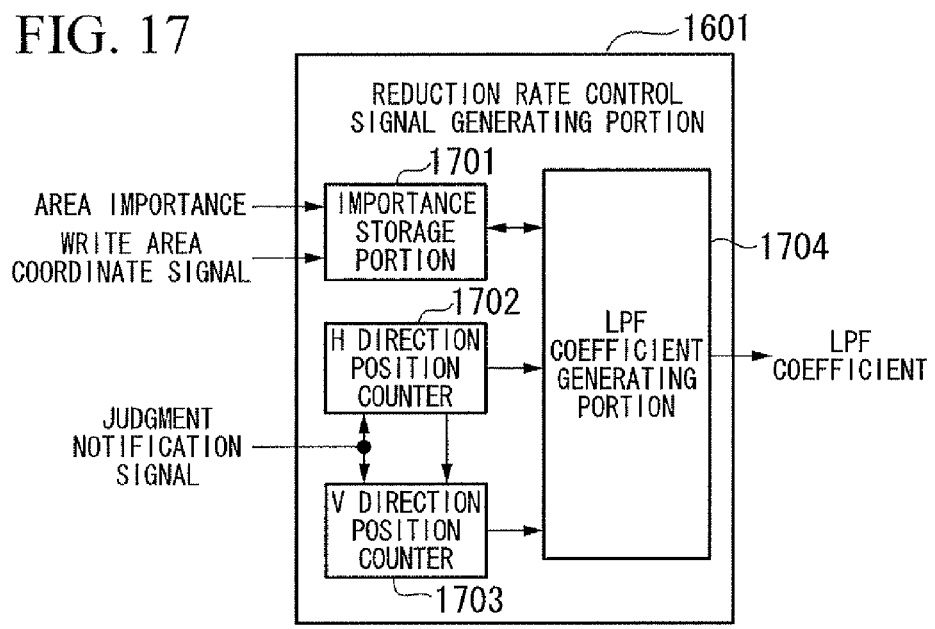
FIG. 17 is a block diagram that shows the constitution of the reduction rate control signal generating portion that is provided in the image processing device in the third embodiment of the present invention.

FIG. 17 shows the constitution of the reduction rate control signal generating portion 1601. An importance storage portion 1701 stores the area importance corresponding to the write area coordinate signal. An H direction position counter 1702 generates an H direction position count value that counts the pixels in the H direction of the processing image. An V direction position counter 1703 generates a V direction position count value that counts the pixels in the V direction of the processing image. An LPF coefficient generating portion 1704 generates an LPF coefficient from the H direction position count value and the V direction position count value.

Next, the operation of the image processing device according to the present embodiment shall be described. The image processing portion 1202 generates the processing image data by performing predetermined image processing on the captured image data that is obtained by the imaging portion 1201, and once writes the processing image data in the processing image data storage portion 1203. At this time, the captured image data is also written in the captured image data storage portion 1204, and after the writing of the captured image data is completed, the captured image data storage portion 1204 generates a write complete notification signal that indicates that the writing of the captured image data has been completed.

Figure 18:
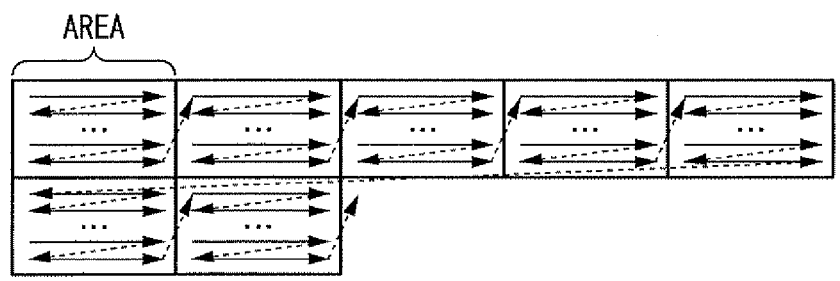
FIG. 18 is a reference diagram that shows the appearance of the reading of captured image data in the third embodiment of the present invention.

Then, the dividing portion 1205 operates as shown below in parallel with the captured image data being read from the captured image data storage portion 1204. When the captured image data is read, the data of each pixel is read in sequence as shown in FIG. 18. The H area pixel counter 1401 in the dividing portion 1205 generates an H area pixel count value that counts the pixels in the H direction in the area by performing a count for each reference timing with the write complete notification signal serving as a start trigger, and performing a reset at each counting of the number of pixels in the H direction of the area. The V area pixel counter 1402 in the same manner generates a V area pixel count value that counts the pixels in the V direction in the area by performing a count for each reference timing with the write complete notification signal serving as a start trigger, and performing a reset at each counting of the number of pixels in the V direction of the area.

The H area counter 1403 generates an H area count value that counts the areas in the H direction in the captured image by performing a count at the timing at which the V area pixel count value is reset with the write complete notification signal serving as a start trigger, and resetting at each counting of the number of areas in the H direction. The V area counter 1404 in the same manner generates a V area count value that counts the areas in the V direction in the captured image by performing a count at the timing at which the H area count value is reset with the write complete notification signal serving as a start trigger, and resetting at each counting of the number of areas in the V direction.

The count value decoder 1405 generates a read address signal for reading processing image data from the processing image data storage portion 1203 at every area similarly to FIG. 18 and a write area coordinate signal that shows the area in the captured image from the H area pixel count value, the H area count value, the V area pixel count value, and the V area count value. The write area coordinate signal changes at every area.

The importance index generating portion 151 in the judging portion 1206 generates an area importance index from the captured image data that is read from the captured image data storage portion 1204, and notifies the generated area importance index to the importance judging portion 1502 at the timing at which the write area coordinate signal changes. Also, the importance index generating portion 1501 resets the generated area importance index when notifying the area importance index to the importance judging portion 1502. The importance judging portion 1502 judges the area importance (for example, one of the three levels of low, medium, high) by comparing the area importance index that is notified from the importance index generating portion 1501 and a plurality of importance judgment threshold values set in advance and generates a judgment notification signal that shows that the importance judgment of all the areas is complete simultaneously with the judgment of the last area.

The importance storage portion 1701 in the reduction rate control signal generating portion 1601 that the reducing portion 1207 is provided with stores the area importance and the write area coordinate signal in correspondence with each other. Then, the reduction rate control signal generating portion 1601 generates an LPF coefficient in the following manner in parallel with the reading of the processing image data from the processing image data storage portion 1203 in accordance with the read address signal.

The H direction position counter 1702 generates an H pixel count value that counts the pixels in the H direction in the processing image by performing a count for each reference timing with the judgment notification signal serving as a start trigger, and performing a reset at each counting of the number of pixels in the H direction of the processing image. The V direction position counter 1703 in the same manner generates a V pixel count value that counts the pixels in the V direction in the processing image by performing a count at the timing at which the H pixel count value is reset with the judgment notification signal serving as a start trigger, and performing a reset at each counting of the number of pixels in the V direction of the processing image.

Figure 19:
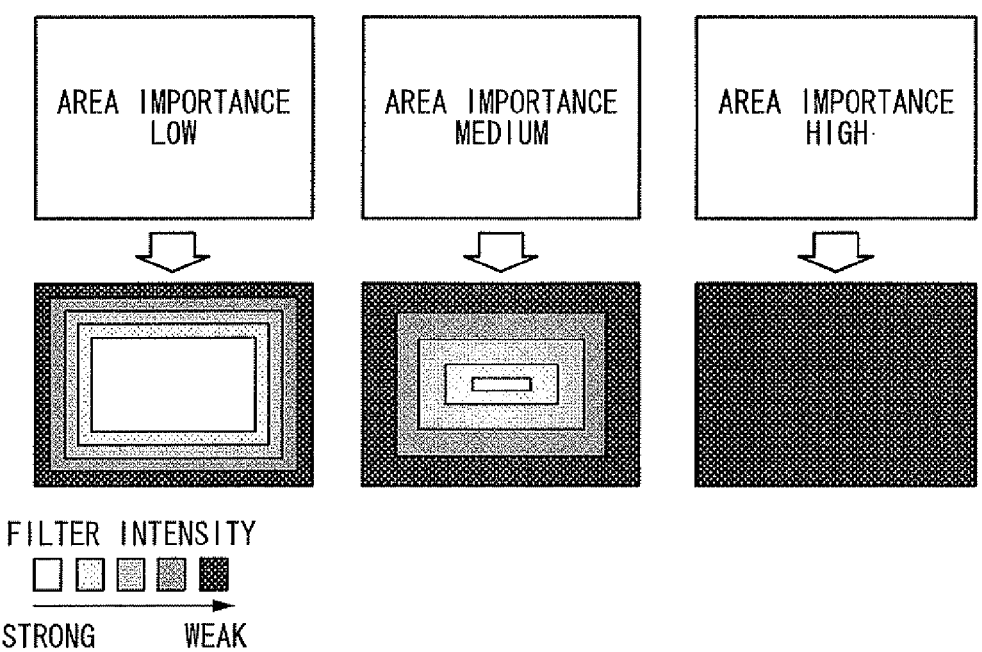
FIG. 19 is a reference diagram that shows the appearance of the LPF coefficient in areas in the third embodiment of the present invention.

The LPF coefficient generating portion 1704 generates a read area coordinate signal that shows the coordinates of the area based on the H pixel count value and the V pixel count value and reads the corresponding area importance from the importance storage portion 1701. Also, the LPF coefficient generating portion 1704 generates an in-area coordinate signal that shows the coordinates in an area based on the H pixel count value and the V pixel count value and, based on the area importance and in-area coordinate signal, generates an LPF signal that sharply changes from weak to strong from the edge to the center of the area when the area importance is "low", generates an LPF signal that gradually changes from weak to strong from the edge to the center of the area when the area importance is "medium", and generates an LPF signal that is uniformly weak over the entire area when the area importance is "high" (refer to FIG. 19).

The reduction processing portion 1602 in the reducing portion 1207 performs data reduction by reduction of the high-frequency component of the processing image data by starting reading of the processing image data from the processing image data storage portion 1203 with the judgment notification signal serving as a trigger, and performing LPF processing of the processing image data in accordance with the LPF coefficient, and thereby obtains reduced image data. The compression portion 1208 generates compressed image data by compressing the reduced image data using JPEG or the like. The transfer portion 1209 transfers the compressed image data from inside the body to outside the body.

As described above, in the present embodiment, LPF processing of the processing image data is executed in accordance with the degree of importance of the captured image. By further raising the intensity of the LPF processing as the degree of importance decreases as in the present embodiment, it is possible to more efficiently reduce the power consumption and time required for transferring the image data to the outside after data reduction, similarly to the first and second embodiments.

Also, by dividing the captured image data into a plurality of areas and judging the degree of importance of each area and then reducing the data amount of the region of the corresponding processing image data in accordance with the degree of importance of each area, it is possible to carry out flexible processing in accordance with the characteristics of each region of the image even when the degree of importance in each region in the image differs. Also, when judging the area importance, by considering the coordinates in the captured image that are indicated by the H direction area count value and the V direction area count value, it is possible to judge the area importance that incorporates a method which makes the center portion of the captured image the important region and the periphery the non-important region.

While preferred embodiments of the invention have been described above with reference to the drawings, specific constitutions of the present invention are not limited to these embodiments, and design modifications with a range that does not depart from the scope of the present invention are included in the present invention. For example, the range of applications of the image processing device of the present invention is not limited to a capsule endoscope.

Also, in the aforementioned embodiments, the data amount was reduced by pixel thinning and LPF processing, but the data amount may also be reduced by changing the compression rate in the compression portion 106, 1208 in accordance with the degree of importance of the image. Moreover, the data amount may be reduced by lessening the number of bits that express one pixel. For example, a pixel that was expressed with 8 bits may be expressed with 4 bits, and two pixels may be expressed with 8 bits.

INDUSTRIAL APPLICABILITY

According to the present invention, by reducing the data amount of a second image data in accordance with the degree of importance of a first image data in an image processing device that compresses image data, it is possible to achieve greater reductions in the data amount as the degree of importance decreases. As a result, it is possible to more efficiently reduce the power consumption and time required when transferring the image data after data reduction.

The invention claimed is:

1. An image processing device, comprising:
   a pre-processing portion that performs a predetermined pre-processing on first image data and outputs it as second image data;
   a judging portion that judges the degree of importance of the first image data on the basis of the characteristics of a subject that is included in the first image data; and
   a reducing portion that reduces the data amount of the second image data in accordance with the degree of importance and outputs it as third image data;
   wherein the judging portion is provided with a judgment data generating portion that generates judgment data for judging the degree of importance of the first image data by calculating a ratio of an average level of color component in the first image data to an expected average level of color component of an observation object.

2. The image processing device according to claim 1, further provided with a dividing portion that divides the first image data into a plurality of areas, wherein the judging portion judges the degree of importance of each of the areas, and the reducing portion reduces the data amount of a corresponding region of the second image data in accordance with the degree of importance of each of the areas.

3. The image processing device according to claim 1, further provided with an image data cutout portion that cuts out a specified area from the first image data, wherein the judging portion judges the degree of importance of the specified area, and the reducing portion reduces the data amount of a corresponding region of the second image data in accordance with the degree of importance of the specified area.

4. The image processing device according to any one of claims 1 to 3, wherein the judging portion is provided with:
   an importance judging portion that judges the degree of importance by comparing the judgment data and a threshold value.

5. The image processing device according to claim 4, wherein the judgment data generating portion generates the judgment data by calculating a ratio of an average level of green color component in the first image data to an expected average level of green color component of the observation object.

6. The image processing device according to claim 1, wherein the reducing portion is provided with:
   a reduction processing portion that reduces the data amount of the second image data; and
   a reduction rate setting portion that sets a reduction rate of the data amount corresponding to the degree of importance for the reduction processing portion.

7. The image processing device according to claim 6, wherein the reduction processing portion thins the second image data at a predetermined ratio, and the reduction rate setting portion sets the predetermined ratio.

8. The image processing device according to claim 6, wherein the reduction processing portion performs low-pass filter processing on the second image data, and the reduction rate setting portion sets a coefficient according to the low-pass filter processing.

9. The image processing device according to any one of claims 6 to 8, wherein the reduction rate setting portion gradually changes the reduction rate from the periphery of an image to the center.

10. The image processing device according to claim 1, wherein:
- the judging portion generates a count value that counts the pixels in a predetermined direction of a pixel data, and generates an enable in relation to pixel thinning of the predetermined direction pixel data from the importance and the count value; and
- the reducing portion reduces a data volume in the predetermined direction at an area of the pixel data corresponding to the enable.

* * * * *